United States Patent [19]
Morgan, Jr. et al.

[11] Patent Number: 4,822,734
[45] Date of Patent: Apr. 18, 1989

[54] METHOD FOR IMPROVING THE ELICITATION OF IgG CLASS MONOCLONAL ANTIBODIES TO TUMOR-ASSOCIATED ANTIGENS AND GLYCOPROTEINS

[75] Inventors: Alton C. Morgan, Jr., Edmonds; Robert McIntyre, Seattle; Clive S. Woodhouse, Edmonds; Paul G. Abrams, Seattle, all of Wash.

[73] Assignee: NeoRx Corporation, Seattle, Wash.

[21] Appl. No.: 773,340

[22] Filed: Sep. 6, 1985

[51] Int. Cl.$^4$ .................. C12P 21/00; C12N 15/00; C12N 5/00; A61K 39/00
[52] U.S. Cl. .................. 435/68; 435/172.2; 435/240.27; 424/85.8; 935/93; 935/108; 530/387; 530/396; 530/413
[58] Field of Search .............. 435/68, 172.2, 240.27; 424/85, 88; 436/548; 935/104, 93, 108; 530/387, 395, 396, 413

[56] References Cited

U.S. PATENT DOCUMENTS

| | | | |
|---|---|---|---|
| 4,372,945 | 2/1983 | Likhite | 424/88 |
| 4,416,866 | 11/1983 | Strand | 436/536 |
| 4,427,653 | 1/1984 | Springer | 435/68 |
| 4,487,833 | 12/1984 | Donahoe et al. | 435/68 |
| 4,720,386 | 1/1988 | McCollester | 424/88 |

OTHER PUBLICATIONS

McMaster et al., European Journal of Immunology 9(6), pp. 426–433 (1979).
Sunderland et al., European Journal of Immunology 9(2) 155–159 (1979).
A. C. Morgan, Jr. and R. A. Reisfeld, Biological Significance of Human Melanoma-Associated Antigens Defined by Xenoantisera, in "Advances in Immunopathology", pp. 299–314, Elsevier North Holland, Inc., 1981.
A. C. Morgan, Jr. et al., "Production and Characterization of Monoclonal Antibody to a Melanoma Specific Glycoprotein", Hybridoma 1:27–35, 1981.
A. C. Morgan, Jr., Monoclonal Antibodies to Human Melanoma-Associated Antigens: Elicitation and Evaluation with Immunochemically Defined Antigen Preparations, in "Melanoma Antigens and Antibodies", pp. 279–288, Plenum Publ. Corp., 1982.
A. C. Morgan, Jr. et al., "Monoclonal Antibodies to Human Colorectal Tumor-Associated Antigens: Improved Elicitation and Subclass Restriction", Hybridoma 3:233–245, 1984.
G. M. Stuhlmiller et al., "D6.1, A Murine Antimelanoma Monoclonal Antibody from Congenitally Athymic Nude Mice Immunized with Purified Melanoma Tumor-Associated Antigen", Hybridoma 3:333–346, 1984.
C. Kordon-Cardo et al., "Immunopathologic Analysis of a Phase I Trial in Patients with Malignant Melanoma", Fed. Proc. 44:8483, 1985.

Primary Examiner—John Edward Tarcza

[57] ABSTRACT

Methods are disclosed for improving the efficiency of elicitation of monoclonal antibodies to glycoprotein antigens and tumor-associated antigens, and for inducing the production of IgG class monoclonal antibodies, in particular the IgG$_3$ subclass. The methods involve the use of a lectin/extract immunogen to stimulate the production of the desired monoclonal antibodies.

10 Claims, 1 Drawing Sheet

TABLE III

| Immunogen | Hybrids | Cultured Cell Evaluation ||| Stable Secreting Clones | Immunoperoxidase Evaluation ||
|---|---|---|---|---|---|---|
| | | Reactivity to Colon Tumor Cells | Nonreactivity to T and B Cells | | Reactivity to Colon Tumor | Nonreactivity to Normal Colon |
| Whole Cells | | | | | | |
| KO-1 | 169 | 4 | 0 (0) | 0 | 0 | 0 (0) |
| KO-2 | 184 | 8 | 0 (0) | 0 | 0 | 0 (0) |
| KO-4 | 300 | 65 | 6 (9) | 2 | 2 | 0 (0) |
| KO-6 | 950 | 128 | 6 (5) | 3 | 1 | 0 (0) |
| KO-7 | 100 | 28 | 3 (9) | 1 | 0 | 0 (0) |
| Membranes | | | | | | |
| FMH 59 | 238 | 31 | 3 (10) | 1 | 1 | 0 (0) |
| FMH 42 | 317 | 48 | 8 (17) | 1 | 1 | 1 (2) |
| Lectin/Extract | | | | | | |
| Lcl | 225 | 28 | 22 (79) | 9 | 9 | 2 (7) |
| WGA | 225 | 71 | 27 (38) | 27 | 27 | 4 (6) |
| DBA | 150 | 55 | 10 (18) | 18 | 15 | 0 (0) |
| PNA | 300 | 34 | 9 (26) | 12 | 11 | 1 (3) |
| Ulex | 376 | 25 | 3 (12) | 0 | 0 | 0 (0) |

METHOD FOR IMPROVING THE ELICITATION OF IgG CLASS MONOCLONAL ANTIBODIES TO TUMOR-ASSOCIATED ANTIGENS AND GLYCOPROTEINS

DESCRIPTION

TECHNICAL FIELD

The present invention relates to methods for the preparation of monoclonal antibodies to glycoproteins in general, and more specifically, to a method for improving the efficiency of elicitation of monoclonal antibodies to tumor-associated antigens, and a method for inducing the production of IgG class monoclonal antibodies.

BACKGROUND ART

The advent of hybridoma technology, originally described by Köhler and Milstein (*Nature* 256: 495, 1975), has made possible the production of antibodies specific to antigens of various cells. Briefly, the production of monoclonal antibodies involves essentially three steps: (a) imminizing a rodent with either intact tumor cells or cell fractions; (b) fusing myeloma cells with spleen cells obtained from the immunized animal in order to produce hybridomas secreting the desired antibody; and (c) culturing the hybridomas and selecting the desired hybridoma clone.

However, not all of the hybridoma clones which result from the procedure described above are directed at the desired antigen. If one utilizes whole tumor cells to induce antibodies to tumor-associated antigens, typically many antibodies are produced to highly immunogenic, non-tumor associated molecules such as histocompatibility antigens or peripheral proteins like fibronectin. If one attempts to reduce the complexity of the immunogen by procedures to enrich or purify certain tumor associated molecules, the immunogenicity of the soluble form of antigen is poor, even when using immunization protocols known to give high-titered antisera in rabbits or goats. Rodents typically require an antigen in an insoluble form. Thus, the number of specifically reactive hybrids obtained is usually low.

Several attempts have been made to narrow the range of monoclonal antibodies elicited. For example, Middleton et al. (*Fed. Proc.* 39: 3464, 1980) disclosed a method of inducing tolerance to B lymphocytes in order to enhance the percentage of T-cell-specific hybridomas. Kennett et al. (*Top. Micro. Immunol.* 81: 77, 1978) describe a method for increasing specificity by blocking surface antigens of one type of cell with whole antiserum to another type of cell not bearing the antigen desired. More recently, U.S. Pat. No. 4,427,653 discloses a method in which antigen mixtures are adsorbed with one or more previously isolated monoclonal antibodies to remove competing immunogenic antigens. Thus, immunogenicity of residual antigens is enhanced due to reduced competition from the depleted antigens.

These methods of immunization are not entirely satisfactory, because either the efficiency of inducing an antibody of choice is low, or because the method requires purified antigen which is difficult to isolate, or requires preexisting monoclonals or polyclonal antisera.

Within the current state of the art, there is particular interest in methods for improving the efficiency of elicitation of monoclonal antibodies to human tumorassociated antigens (TAA). Most of the research efforts have involved the use of intact tumor cells for both the elicitation and evaluation of hybridoma products.

Also of interedst are methods of inducing monoclonal antibodies of the IgG class, in particular the $IgG_3$ subclass. Recent reports with the $IgG_3$ monoclonal antibody to the glycolipid antigen $GD_3$ have indicated that monoclonal antibodies mediating antibody-dependent cellular cytotoxicity (ADCC) in vitro may also mediate anti-tumor effects in patients receiving these unconjugated monoclonal antibodies (Cardon-Cardo et al., *Fed. Proc.* 44: 8483, 1985). In contrast, monoclonals of other subclasses do not mediate ADCC as effectively. Monoclonal antibodies of the $IgG_3$ subclass are, however, typically very rare in fusions generated from whole-cell immunizations.

There exists a need in the art, then, for methods of inducing the production of IgG-class monoclonal antibodies, in particular the $IgG_3$ subclass, as well as a method for improving the efficiency of elicitation of monoclonal antibodies to glycoproteins and, in particular, tumor-associated antigens. The present invention fulfills these needs and further provides other related advantages.

DISCLOSURE OF INVENTION

Briefly stated, the present invention discloses a method for improving the efficiecy of elicitation of monoclonal antibodies to glycoprotein antigens, comprising (a) immunizing an animal with a lectin/extract immunogen; (b) fusing spleen cells from the immunized animal to myeloma cells to form hybridomas capable of producing MAbs to the particular glycoprotein; (c) culturing the hybridomas to produce the MAbs; and (d) collecting the antibodies as a product of the hybrids. A second aspect of the present invention discloses a method for inducing the production of IgG class monoclonal antibodies, including a highly efficient method of inducing those of the $IgG_3$ subclass. The method involves the steps of (a) immunizing an animal with a lectin/extract immunogen; (b) fusing spleen cells from the immunized animal to myeloma cells to form hybridomas capable of producing IgG class monoclonal antibodies; (c) culturing the hybridomas to produce the IgG class monoclonal antibodies; and (d) collecting the antibodies as a product of the hybrids. A method for improving the elicitation of monoclonal antibodies to tumor-associated antigens is also disclosed.

Monoclonal antibodies produced by the methods described herein are also disclosed, and in particular, monoclonal antibodies of the IgG class produced by a hybridoma formed from the fusion of cells from a myeloma line and spleen cells from a rodent previously immunized with a lectin/extract immunogen.

These and other aspects of the invention will become apparent upon reference to the following detailed description and attached drawing.

BRIEF DESCRIPTION OF THE DRAWINGS

The figure is a table giving examples of the comparative evaluation of lectin/extracts versus whole-cell and membrane immunogens.

BEST MODE FOR CARRYING OUT THE INVENTION

The inventor herein has previously produced and characterized a monoclonal antibody (MAb) to a melanomaassociated glycoprotein (Morgan et al., *Hybridoma* 1: 27–35, 1981). This previous work dealt with the elicitation of MAb's to antigens shed into the culture medium by human melanoma cells. In particular, MAb's were developed against a 240kd melanoma-associated antigen (MAA). One particular feature of the 240kd MAA which aided the isolation of MAb's to this protein was its selective affinity for lens culinaris lectin. Since the 240kd component bound to this particular lectin, the lectin could be used as a tool to isolate this particular component. This resulted in (1) the enrichment of the 240kd MAA, and (2) a reduction in the level of immunodominant antigens, such as HLA-A,B,C, HLA-DR, and fibronectin. This original research demonstrated that MAb could be elicited to a particular MAA by taking advantage of its biochemical properties.

Within the present invention, the inventor has discovered that immunization with tumor extracts absorbed to insolubilized lectins is a general method for increasing the efficiency of generating antibodies to tumor-associated antigens, and further, may be used as a method for generating antibodies of restricted subclass distribution, as compared with immunogens derived from isolated tumor cells or membranes or xenografted tumors.

More specifically, the use of Sepharose-bound lectins combined with peripheral protein extracts of heterotransplanted tumors is superior to the use of other types of immunogens in two areas: (1) the number of hybrids reactive with tumor cells or extracts, but not with lymphoid cells or extracts; and (2) the number of hybrids reactive with tissue sections of tumors, but not normal tissue sections.

A number of factors may contribute to the superiority of lectin/extract immunogens for the production of antibodies to tumor-associated antigens (TAA). First, peripheral protein extracts using agents such as LIS (lithium diiodosalicylate) of both melanoma and colon do not contain detectable histocompatibility antigens, but are enriched in peripheral membrane components. Thus, antibodies to these integral histocompatibility glycoproteins which are highly immunogenic in xenoimmunization would not be elicited, allowing a heightened response to potentially less immunogenic tumor associated antigens. In addition, separation of glycoprotein and glycolipid species by absorption to lectins might be expected to lead to further enrichment of certain glycoprotein tumor-associated antigens.

A second possible reason for the superiority of lectin extracts could be the source of the extract. Cells cultured in media containing fetal calf serum acquire immunogenic proteins from the supplement and, in a similar manner, cells harvested from surgical specimens may bear adsorbed serum proteins. Since the extracts within the present invention were made from nude mouse xenografts, adsorbed serum proteins would be of mouse origin and presumably less immunogenic in mice. Finally, lectins themselves may have some adjuvant effect and potential for targeting to sensitized lymphoid cells.

Not only is the method of the present invention more efficient in eliciting antibodies to tumor associated antigens, but also represents a novel methodology for inducing MAbs of IgG subclasses, in particular ones of the $IgG_3$ subclass. In contrast, many antibodies elicited by whole tumor cells are typically IgM or $IgG_1$. Noting that MAbs of the $IgG_3$ subclass mediate antibody-dependent cellular cytotoxicity more effectively, the antibodies produced by the method of the present invention may be useful in eliciting MAbs which can be effective in unconjugated form for the therapy of cancer.

By way of example, the use of lectin/extract immunogens has been shown to be a generally useful immunization procedure for human colorectal cancer. In addition, the inventor has utilized this methodology to elicit antibodies to non-small cell lung cancer. Similar to the results with colon cancer, a large number of antibodies were elicited which reacted to lung cancer cells of both adeno and large cell origin but not to a pool of B-cell and T-cell lymphoid cells. The antibodies from these fusions are still undergoing characterization against a large battery of both normal and tumor tissues. Similarly, the inventors have utilized LIS extract/lectin immunogens to raise antibodies to ovarian cancer. Through the first screen, 30 percent of all antigen reactive wells reacted specifically with ovarian cancer cells, but not a B and T cell pool. Thus, the results in lung and ovarian cancer, as well as colon cancer, have demonstrated that the immunization procedure is applicable to most tumor types.

The current invention, then, would be applicable to any tumor that could be transplanted and grown in nude mice. It would also be apparent to one skilled in the art to utilize extract sources other than nude mouse tumors. The inventor has also utilized peripheral protein extracts from cultured cells grown in chemically defined medium in order to eliminate the presence of fetal calf serum proteins contaminating the extract. The use of chemically defined spent culture medium would allow the same advantages of not having competing non-tumor-specific, serum-derived proteins within the immunogen.

The inventor has utilized, by way of example, extracts from tumor cells grown in either chemically defined medium or heterotransplanted into nude mice. The extracts, regardless of the agent used for extraction, have similar properties, i.e., they are devoid of integral membrane components and such immunogenic constituents as histocompatibility antigens. Second, these extraction techniques represent non-detergent extracts which would therefore leave behind many glycolipids. Thus, only peripheral glycoproteins and gangliosides should be present in these extracts. Extracting agents useful in this regard have been shown to be lithium diiodosalicylate (LIS) or isotonic urea. Other selective peripheral protein extraction agents may be utilized, including butanol, which has been previously described in a mouse tumor system. Peripheral protein extraction can also be accomplished by using low concentrations of non-ionic detergents for long periods of time, i.e., 0.01% NP-40 for four hours. In the latter case, the low concentration of the detergent is not sufficient to extract integral proteins. Similarly, extracts such as perchloric acid, as used in CEA extractions, may also be utilzied.

Lectins which may be used within the description of the present invention include lens culinaris, wheat germ agglutinin, peanut agglutinin, Dolichos biflorus agglutinin, Con A and Ulex europeaus I agglutinin. A variety of other lectins with differing sugar specificities may also be useful in the current mode of this invention. However, elicitation of monoclonal antibodies to tumor-associated antigens rather than to glycoproteins in general may be increased by utilization of particular lectins which seem to show some specificity to tumor cells versus normal cells. The best example of these types of lectins is wheat germ agglutinin (WGA), which has been shown by a number of investigators working with mouse melanoma cells to bind to metastatic but not non-metastatic variants of B16 mouse melanoma. The lectin seems to select for cells expressing a cell surface glycoprotein important in the metastatic process. Similarly, studies by other investigators have shown that certain lectins, like peanut agglutinin, can bind specifically to colon tumor cells and not to normal colonic mucosa. Thus, one may be able to combine the specificity of the lectin together with its general property of binding glycoproteins and thus enhancing the immunogenicity of soluble antigens.

In raising MAbs to glycoproteins in general, it is preferable to have previously ascertained the glycoprotein's lectin binding properties. For example, it is known that carcinoembryonic antigen (CEA) binds to WGA lectin. By adsorbing a LIS extract of colon tumor cells with insolubilized WGA, the inventors elicited over thirty anti-CEA antibodies of 192 antigen reactive wells. The lectin binding characteristics can be ascertained for many glycoprotein through a variety of standard techniques. Typically, adsorption with a panel of lectins, followed by SDS-PAGE for visualization, if the extract is radiolabeled, or by solid phase ELISA on extract fractions (non-adsorbed and eluate) if a previous polyclonal or monoclonal antibody exists.

The process of the present invention begins with the extraction of peripheral membrane components from cells and continues with the characterization of the extracts with known monoclonal antibodies to either integral or peripheral protein components. Subsequently, the peripheral protein extract is bound to appropriate lectins insolubilized on Sepharose particles, and the combination used to immunize mice in a weekly protocol scheme. Fusions and hybrid selection were done according to well-known and published techinques. Screening of hybridomas was carried out not only against whole-cell antigen targets, but against the extracts used for immunization and similar extracts prepared from control cells.

Examples of the comparative evaluation of lectin extracts versus whole-cell and membrane immunogens are shown in the Figure. As a corollary to these studies, it was shown that a particular tumor-associated antigen, carcinoembryonic antigen (CEA), is also more immunogenic when insolubilized from peripheral protein extracts onto lectins. Finally, subclass determinations are shown on a variety of lectin immunogens, demonstrating that both the Dolichos biflorus and peanut agglutinin immunogens were highly specific in eliciting the $IgG_3$ subclass. It is evident that the peripheral protein extract/lectin immunogen effective in immunizing mice and rats would also be effective in eliciting tumor-associated responses in other mammalian species and further could be useful as a vaccine approach.

The following examples are offered by way of illustration and not by way of limitation.

EXAMPLE 1

Extraction of Membrane Proteins

The immunogen source was derived from colon tumors implanted in nude mice. Tumor cell membranes were prepared with a motorized Dounce homogenizer in 0.01 M Dulbecco's phosphate-buffered saline with 10 units/ml of DNase I and 0.1% aprotinin (PBS-H) (Sigma Chemical Co., St. Louis, MO). The membranes were then incubated at 37° C. for 30 min, layered onto 41% sucrose/phosphate buffered saline, and centrifuged at 100,000 x g for 60 min; crude membranes were isolated at the interface. (Howard et al., *J. Immunol. Meth.* 38: 75, 1980).

Crude membranes were pooled from xenografts of four different patients' tumors and were extracted with 2.5 mM lithium diiodosalicylate (LIS) (Pearson et al., *Cancer Immunol. Immunother.* 11: 173, 1981) in diluted PBS (0.001M) for 60 min at 25° C. and then for an additional 60 min at 4° C. complete the extraction. The degree of integral protein extraction was assessed by binding with MAb to framework determinants of HLA-A,-B, and -C antigens in solid-phase ELISA (Morgan, Jr., A.C. and McIntyre, R.F., *Cancer Res.* 43: 3155, 1983), as previously described by the inventor (Morgan et al., *Hybridoma* 1: 27, 1981). The presence of peripheral proteins in the extract was monitored by binding with MAb to CEA (Gatter, et al., *J. Clin. Pathol.* 35: 1253, 1982). The residual membranes were then solubilized in either 1% NP-40 or 0.5% Lubrol-WX (Sigma) and used as solid phase targets in ELISA to determine the presence of integral membrane components.

Conjugation of Membrane Proteins with Lectins

Ten milligrams (total protein) of the extracts were absorbed to 250 ul, packed volume, of Sepharose-bound lens culinaris lectin (LCL), wheat germ agglutinin (WGA), peanut agglutinin (PNA), Ulex europeaus I agglutinin (UEA), or Dolichos biflorus agglutinin (DBA) (Vector Laboratories, Burlingame, CA) which were typically conjugated at 2mg/ml. Lectin immunosorbents were then incubated at 4° C. for 2 hours and then extensively washed with PBS.

Preparation of Hybridomas

The lectin/extracts were injected once per week intraperitoneally for six weeks and spleens were harvested on the third or fourth day after the last injection. For serologic assessments, LIS or Lubrol extracts were extracted wtih chloroform/methanol (Folch et al., *J. Biol. Chem.* 226: 497, 1957), and the glycolipid used to assess binding of hybridoma supernates (Brockhaus et al., *J. Biol. Chem.* 256: 13223, 1981).

Fusion was carried out at a 10:1 ratio of spleen cells to NS-1 mouse myeloma cells using 50% PEG 1000. Alternatively, Sp2/0 cells or $P_3Ag8X653$ cells may be used. Hybrids were selected in hypoxanthine, aminopterin, and thymidine supplemented medium using either a 24-well technique (Gefter et al., *Somatic Cell Genet.* 3: 231, 1977), or a 96-well technique (Littlefield, J.W., *Science* 145: 709, 1964). Selected hybridomas were cloned by a limiting dilution technique on feeder layers of freshly isolated three-to-four-week-old thymocytes or in wells supplemented with spent culture medium of NS-1. All fusions, regardless of the immunogen, resulted in an average of 3 hybrids/2.5 x 105 cell/well in the 96-well technique. All wells were also assayed for murine immunoglobulin production (Morgan et al., *J. Immunol. Meth.* 39: 223, 1980). Cell fusions resulted in 70%-90% hybridoma positive wells.

Screening of Hybridomas

For initial screening of hybridoma supernates, either an indirect 125 I-Protein A assay (Rockoff et al., *J. Immunol. Meth.* 26: 369, 1979) or a biotin-avidin ELISA (Morgan, Jr., A.C. and McIntyre, R.F., *Cancer Res.* 43: 3155, 1983) was utilized. Each fusion was screened against glutaraldehyde-fixed cultured colon tumor cells, and pooled B and T cells. LIS or Lubrol extracts from colon tumor xenografts were also used for selection. Charcterization of cloned hybridomas versus purified blood group substances, pooled red blood cell membranes, glycolipid preparations, or cultured cells was accomplished by biotin-avidin ELISA or horseradish peroxidase-conjugated antiglobulin ELISA (Morgan, Jr., A.C., and McIntyre, R.F., Cancer Res. 43: 3155, 1983).

Subclass determinations were made on spent culture medium of doubly cloned hybrids by a sandwich ELISA (Morgan et al., J. Immunol. Meth. 39: 233, 1980) utilizing subclass-specific reagents for detection (Litton Bionetics, Kensington, MD). Subclass determinations were performed at least two times.

A summary of the results of the fusions is given in the Figure. The number of wells or colonies reactive with tumor cells varied between 7% -37% with the lectin extracts. The results shown are from one fusion with each lectin/extract combination. However, in each case, the type of immunogen was repeated at least once, and in most cases three times. In each immunogen, a fusion utilized the spleen cells of one mouse. Each lectin/immunogen required 3-6 weekly immunizations for optimal antibody elicitation. However, antibodies could be elicited with PNA/extract immunogens with only a single immunization.

The two major types of antigens recognized by MAbs elicited by colorectal tumor cells were glycolipid or glycoproteins with blood group specificities or CEA. Stable cloned hybridomas which were elicited by various lectin/extract combinations were evaluated for rectivity to both glycoproteins bearing blood group specificities and to purified CEA.

Referring now to Table 1, a summary of the blood group reactivity of the antibodies elicited by the various immunogens is shown.

TABLE 1

| Category of Monoclonal Antibody | Lectin Used in Immunogen | | | |
|---|---|---|---|---|
| | LCL | WGA | DBA | PNA |
| CEA only | 0 | 7 | 0 | 0 |
| $Le^a$ only | 0 | 0 | 2 | 0 |
| $Le^a$/CEA | 1 | 1 | 10 | 5 |
| A,B,H/$Le^a$/$Le^b$/CEA | 2 | 3 | 6 | 2 |
| Non-blood group-non-CEA | 5(63)[b] | 9(38)[b] | 2(11)[b] | 3(25)[b] |

[a] Only stable secreting clones from Table 1 were assayed. Clones were derived from two separate fusions with each lectin/extract.
[b] Percentage of total.

As shown in Table 1, DBA/LIS was the most effective immunogen in eliciting $Le^a$/CEA cross-reactive antibodies. The DBA/LIS and PNA/LIS immunogens produced the highest proportion of antibodies reacting with blood group specificities or CEA. In addition, PNA/LIS was the only immunogen which produced an antibody which reacted equally well with $Le^a$ or CEA, but not to glycoproteins with other blood group specificities. These results indicate that the type of lectin utilized to absorb molecules from the heterogeneous peripheral protein extract will dictate to some extent the specificity of the elicited antibody, but that certain antibody specificities were elicited regardless of which lectin was utilized.

Isotype and subclass patterns were also examined for antibodies elicited with the different lectin/LIS extract combinations. The class and subclass distribution of the monoclonal antibodies is shown in Table 2.

TABLE 2

| Class or subclass | Lectin Used in Immunogen | | | |
|---|---|---|---|---|
| | LCL | WGA | DBA | PNA |
| IgM | 2 | 3 | 1 | 0 |
| $IgG_1$ | 3 | 10 | 2 | 1 |
| $IgG_{2a}$ | 1 | 4 | 0 | 0 |
| $IgG_{2b}$ | 0 | 3 | 0 | 2 |
| $IgG_3$ | 1 | 0 | 13 | 9 |

As shown in Table 2, 75% to 80% of the antibodies elicited with either DBA/LIS or PNA/LIS were $IgG_3$, whereas the LCL/LIS and WGA/LIS immunogens elicited antibodies with a wide range of isotypes and subclasses. Only 13% of all of the antibodies examined were IgM.

EXAMPLE 2

Tumor Vaccines

Since lectin immunogens combined with peripheral protein extracts have shown utility in generating tumor-associated responses in mice, the same sort of responses may be generated in patients for which these immunogens have been prepared. In particular, lectin immunogens combined with selective protein extractions could prove useful as vaccines in more effective elicitation of anti-tumor responses. Current vaccines employing cultured tumor cells or patient tumor cells with adjuvants do not as a rule elicit tumor-specific responses. The explanation for this may be that whole tumor cells represent a large repertoire of antigens, including non-tumor-associated antigens, and together with adjuvants one may induce antibodies to these non-tumor-specific components. Further, the tumor-associated components may not be presented in an optimally immunogenic fashion. A combination of a selective extraction technique with a particular lectin may present to a patient's immune response only a selected group of glycoproteins.

As an example one might postulate that a patient's colon tumor, resected during surgery, might be used for subsequent adjuvant therapy. Conceivably one would prepare an extract of the colon tumor as indicated above with an agent such as LIS. The extract could then be adsorbed to, preferably, peanut agglutinin bound to Sepharose. After removing non-adsorbed proteins, the patient could be immunized subcutaneously on a weekly basis. Periodically, both delayed hypersensitivity reactions and humoral responses could be monitored versus LIS extracts of tumor and normal colon along with tumor responses. Peanut agglutinin was chosen because it has been shown to bind specifically to colon tumors but not normal colon on tissue sections. However, other lectins might prove useful when combined with the selective extraction technique. The immunization protocol would also be advantageous because few approved adjuvants exist for use in humans and the lectin itself could play the role as adjuvant.

From the foregoing it will be appreciated that, although specific embodiments of the invention have been described herein for purposes of illustration, various modifications may be made without deviating from the spirit and scope of the invention. Accordingly, the invention is not limited except as by the appended claims.

We claim:

1. A method for improving the efficiency of elicitation of IgG$_3$ monoclonal antibodies to peripheral membrane protein antigens, comprising:

preparing a periperal protein extract of crude cell membranes, thereby forming an antigenic extract;

adsorbing the antigenic extract to a lectin immunosorbant wherein the lectin is selected from the group consisting of Dolichos biflorus agglutinin and peanut agglutinin, thereby forming a lectin-extract immunogen;

immunizing an animal with the lectin-extract immunogen;

fusing spleen cells from the immunized animal to myeloma cells to form IgG$_3$-secreting hybridomas capable of producing monoclonal antibodies directed against a peripheral membrane protein antigen;

culturing the hybridomas to produce IgG$_3$ monoclonal antibodies; and collecting the IgG$_3$ monoclonal antibodies as a product of the hybrids.

2. The method of claim 1 wherein the antigenic extract is derived from crude membranes prepared from either cultured cells grown in chemically defined medium; spent culture medium; xenografted tumors; normal tissue; or tumor tissue.

3. The method of claim 2 wherein the tumor tissue is colon, lung or ovarian adenocarcinoma.

4. The method of claim 3 wherein the extract is a lithium diiodosalicylate antigenic extract of peripheral membrane proteins.

5. The method of claim 1 wherein said myeloma cells are NS-1 cells, Sp2/0 cells or P$_3$Ag8X653 cells.

6. The method of claim 1 wherein said antigenic extract is an extract of spent culture medium from cells cultured in chemically defined medium or cells cultured in serum-supplemented medium.

7. The method of claim 1 wherein said antigenic extract is isolated from nude mouse xenografts.

8. The method of claim 1 wherein said animal is selected from the group consisting of mice and rats.

9. The method of claim 1 wherein said lectin is peanut agglutinin and said animal requires no more than two injections with said immunogen.

10. The method of claim 1 wherein the antigenic material includes a tumor-associated antigen.

* * * * *

UNITED STATES PATENT AND TRADEMARK OFFICE
CERTIFICATE OF CORRECTION

PATENT NO. : 4,822,734
DATED : April 18, 1989
INVENTOR(S) : Morgan, Jr. et al.

It is certified that error appears in the above-identified patent and that said Letters Patent is hereby corrected as shown below:

| | | |
|---|---|---|
| Column 2, | line 3: | "interedst" is changed to --interest--. |
| Column 2, | line 67: | "melanomaassociated" is changed to --melanoma-associated--. |
| Column 6, | line 10: | after "4° C." insert --to--. |
| Column 6, | line 57: | "2.5 x 105" is changed to --2.5 x $10^{-5}$--. |
| Column 10, | line 4: | "claim 2" is changed to --claim 1--. |
| Column 10, | line 6: | "claim 3" is changed to --claim 1--. |
| Column 10, | line 6: | after "wherein the" insert --antigenic--. |
| Column 10, | line 7: | after "diiodosalicylate" delete --antigenic--. |
| Column 10, | line 23: | "material" is changed to --extract--. |

Signed and Sealed this

Eighteenth Day of December, 1990

Attest:

HARRY F. MANBECK, JR.

*Attesting Officer*   *Commissioner of Patents and Trademarks*